US005677424A

United States Patent [19]

Rucheton et al.

[11] Patent Number: 5,677,424
[45] Date of Patent: Oct. 14, 1997

[54] METHOD FOR PURIFYING AN AQUEOUS SOLUTION OF RAW ALBUMIN

[76] Inventors: Marcel Rucheton, 10, rue de la Confrérie, 34000 Montpellier; Elie Stefas, 94, allée des Fauvettes, 34280 La Grande Motte; Hubert Graafland, 10 A, avenue du Professeur Grasset, 34000 Montpellier, all of France

[21] Appl. No.: 325,277

[22] PCT Filed: Apr. 22, 1993

[86] PCT No.: PCT/FR93/00395

§ 371 Date: Oct. 24, 1994

§ 102(e) Date: Oct. 24, 1994

[87] PCT Pub. No.: WO93/21228

PCT Pub. Date: Oct. 28, 1993

[30] Foreign Application Priority Data

Apr. 22, 1992 [FR] France .................................. 92/04941

[51] Int. Cl.$^6$ .................................. C07K 1/00; A23J 1/00; B01D 15/08
[52] U.S. Cl. .......................... 530/364; 530/362; 530/363; 530/412; 530/416; 530/417; 530/418; 530/427; 210/645; 210/651; 210/656; 210/660
[58] Field of Search .................................. 530/364, 362, 530/363, 412, 416, 417, 418, 427; 210/656, 660, 651, 645

[56] References Cited

U.S. PATENT DOCUMENTS

| 4,855,055 | 8/1989 | Lui et al. ............................ 530/413 |
| 5,094,960 | 3/1992 | Bonomo ............................ 436/178 |
| 5,169,936 | 12/1992 | Staples et al. ........................ 530/350 |
| 5,250,662 | 10/1993 | Chang .............................. 530/364 |

FOREIGN PATENT DOCUMENTS

| 0319067 | 7/1989 | European Pat. Off. . |
| 0366946 | 9/1990 | European Pat. Off. . |

OTHER PUBLICATIONS

Wichman et al, *Biochemica et Biophysica Acta*, vol. 372, No. 1, pp. 218–224, 1974.
Scopes, "Protein Purification—Principles and Practice", Springer–Verlag, pp. 176–179, 1987.
Wichman et al, "Purification of human serum albumin by affinity chromatography", Biochimica et Biophysica Acta, vol. 372, No. 1, 1974, pp. 218–224.
Krizanova et al, "Application of a new hydrophobic carrier for routine isolation of calmodulin and other proteins", General Physiology and Biophysics, vol. 5, No. 2, 1986, pp. 201–204.

*Primary Examiner*—Cecilia J. Tsang
*Assistant Examiner*—Abdel A. Mohamed
*Attorney, Agent, or Firm*—Cushman Darby & Cushman Intellectual Property Group of Pillsbury Madison & Sutro LLP

[57] ABSTRACT

Method for purifying an aqueous solution of raw albumin wherein contaminant proteins are bound by chromatography to a stationary solid phase, preferably a particulate phase, the purified albumin solution being collected as an effluent, in which a neutral phase charged with at least one compound chosen from the group formed by compounds containing $C_3$ to $C_8$ alkyl radicals and compounds containing sulfate groups is used as the stationary phase.

18 Claims, 2 Drawing Sheets

5,677,424

METHOD FOR PURIFYING AN AQUEOUS SOLUTION OF RAW ALBUMIN

BACKGROUND OF THE INVENTION

1. Field of the Invention

The invention relates to a method for purifying an aqueous solution of raw albumin.

The solution may be any aqueous solution of raw albumin. It is more particularly an albumin solution obtained from the blood plasma of a mammal such as a bovine, horse, pig, sheep or rabbit and preferably a solution obtained from human plasma.

2. Description of the Related Art

It is well known to separate out from blood, by centrifugation, on the one hand, the globules and, on the other hand, the blood plasma. It has for many years been known that the plasma contains, besides albumin which constitutes the majority of the dissolved material, a whole series of other molecules, in particular proteins, the extraction of which is particularly valuable bearing in mind their therapeutic uses. Methods have thus been proposed for fractionated precipitation by a precipitation agent at variable pH, ionic strengths and temperature. The process which is currently the most widely used is that of Cohn (see COHN J. et al. J. Am. Chem. Soc. 72, 465–474/1950) or variants of this process in which the precipitation agent used is ethanol. According to the said Cohn process, the plasma is cooled to −30° C. and then warmed to +2° C., which thereby results in a cryoprecipitate containing anti-hemophilia factor VIII, fibrinogen and fibronectin. The supernatant, referred to as "supernatant I", is separated from the abovementioned precipitate; its pH is lowered to 5.85±0.05 and ethanol is added until the ethanol concentration is 19 % by volume, the temperature being lowered, progressively as the ethanol is added, to −5° C. A precipitate is thus obtained, referred to as "precipitate (II+III)", containing in particular the gamma-globulins and a supernatant, referred to as "supernatant (II+III)" containing the albumin and impurities. The supernatant thus obtained is taken up and the alcohol content is increased until an ethanol concentration of 40% by volume is obtained, the temperature being lowered to approximately −8° C. A precipitate is thus obtained, referred to as "precipitate IV", and a supernatant, referred to as "supernatant IV", which contains the albumin with a degree of purity of approximately 94 to 97% by weight of proteins. Supernatant IV serves as starting material for the desired albumin solutions, but it contains a large amount of ethanol; according to a first technique, supernatant IV may be dialysed directly against physiological serum, but it is then necessary to use a very large amount of water and the method is thus slow and expensive; according to another technique, the pH of supernatant IV is lowered to 4.80±0.05, which causes the albumin to precipitate: this precipitate, referred to as "precipitate V", is separated out and is redissolved in physiological serum, the remainder of the ethanol being extracted by dialysis.

To complete the purification of albumin, it has already been proposed to use chromatographic techniques, in particular by ion exchange (see in particular Curling J. M., Methods of Plasma Protein Fractionation, Ed. J. Curling, Acad. Press, 77–91 (1980); Tayot J. L. et al., Methods of Plasma Protein Fractionation, Ed. J. Curling, Acad. Press, 149–160 (1980); Saint-Blancard J., Nouveaux échangeurs d'ions Trisacryl [Novel Trisacryl ion exchangers], Ann. Pharm. Fr. 39, 403–409 (1981)). The principle behind these methods is to bind the albumin to a specific support, as a function of the pH and of the ionic strength, and thereby to eliminate in the effluent some of the impurities which are found in the albumin solution treated by chromatography. Unfortunately, although these techniques allow the quality of the albumin solutions obtained to be enhanced substantially, they are difficult and expensive to implement. In actual fact, the treated albumin solutions contain approximately 4% of diverse impurities to be extracted. Given that the albumin is bound to the packing material of the chromatography column, it is necessary to bind 96% of the material treated and, since the binding of albumin per gram of packing material is limited, of an order of magnitude of approximately 10 mg, this involves the use of a very large packing bed volume in the columns. Given that the packing material is very bulky, the implementation requires a large amount of water to ensure, on the one hand, pre-equilibration of the column and, on the other hand, passage of the product on the column; in addition, the nature of the packing materials used generally requires, for the pre-equilibration, the use of special buffers. Moreover, when the albumin has been retained on the bed of packing material, it is necessary, in order to recover it, to elute it from the column using suitable solution-buffers, such that the albumin is subsequently found mixed with these buffers and that it is advisable to redialyse the albumin solutions in order to eliminate the solution-buffer salts and to obtain finally an injectable product.

It is also known, for example from EP-A 0 367 220, to separate out the impurities by passage on a DEAE-SEPHADEX column or on a column of SEPHAROSE 4B activated with cyanogen bromide and on which are bound specific antibodies, impurities such as haptoglobin and $\alpha_1$-AGP binding to the column and the effluent consisting of purified albumin. This type of chromatography is advantageous because, firstly, only the impurities should be retained on the chromatography column, which allows packing beds of reduced volume to be used; secondly, the volume of effluent containing the albumin is also reduced and is, in fact, of the order of the initial loading volume; thirdly, the pre-equilibration of the columns thereby requires only smaller amounts of liquid; in the fourth place, there is no need to wash the packing beds completely and as a precaution for recovery of the albumin and, in the fifth place, simple washing is sufficient to regenerate the chromatography columns, without the need for any great precautions for the washing processes. However, the albumin obtained may still, under hot conditions, form excessively large amounts of polymers.

SUMMARY OF THE INVENTION

The subject of the present invention is a purification method in which the impurities are bound by chromatography, the effluent consisting of a solution of albumin, which allows a very pure albumin forming practically no polymers under hot conditions to be obtained.

The present invention relates to a method for purifying an aqueous solution of raw albumin wherein contaminant proteins are bound by chromatography to a stationary solid phase, the purified albumin solution being collected as an effluent, characterized in that a neutral phase, or one in the region of neutrality, charged with at least one compound chosen from the group formed by compounds containing $C_3$ to $C_8$ alkyl radicals and compounds containing sulfate groups is chosen as the stationary phase.

The stationary solid phase may be in the form of fibers or membranes; it preferably consists of a neutral particulate material, that is to say one which is generally considered as neutral in chromatography and the particles of which have an average size of less than 2 mm, preferably between 1 µm and 2 mm. In this case, the chromatography is carried out on at least one column.

The raw aqueous solution of albumin is preferably a solution obtained from blood plasma, in particular human plasma, by a known process of COHN type, according to which the said plasma is fractionated by successive treatments by modifying the temperature and by the action of the precipitation agent in order to obtain, after at least partial separation of the factors VIII and IX and of the γ-globulins, albumin solutions in order to extract the precipitation agent and to collect the raw albumin solution.

The raw aqueous solution of albumin advantageously has a raw albumin concentration of between 1 g and 300 g per liter and has a pH between 6 and 8, preferably between 6.9 and 7.1.

The compound containing $C_3$ to $C_8$ alkyl radicals with which the stationary phase is charged is preferably a butyl radical. The packing bed of the chromatography column(s) then consists, in particular, of the product marketed by the company MERCK under the tradename FRACTOGEL TSK.BUTYL-650 (a gel containing butyl groups linked to an hydrophilic polyvinyl gel).

The compound containing sulfate groups with which the stationary phase is charged is preferably a dextran sulfate. The packing bed of the chromatography column(s) consists, in particular, of the product marketed under the tradename DEXTRAN BEADS SULFATED by the company SIGMA (size exclusion gel filtration media of crosslinked dextran and acrylamide).

According to the present invention, the raw aqueous solution of albumin is preferably subjected to at least two chromatographies, at least one being a chromatography on a stationary phase charged with a compound containing $C_3$ to $C_8$ alkyl radicals and at least one other being a chromatography on a stationary phase charged with a compound containing sulfate groups.

Advantageously, the raw aqueous solution of albumin is subjected to a chromatography on a stationary phase charged with a compound containing sulfate groups, before and after a chromatography on a stationary phase charged with a compound containing $C_3$ to $C_8$ alkyl radicals or, conversely, to a chromatography on a stationary phase charged with a compound bearing $C_3$ to $C_8$ alkyl radicals, before and after a chromatography on a stationary phase charged with sulfate groups.

The effluents from a first chromatography may advantageously be used directly to supply the next chromatography. The chromatography temperature is from 1 to 30° C. The column chromatography flow rate is generally between 1 and 30 cm/hour.

If necessary, the pH of the aqueous solution of albumin obtained as the final chromatography effluent is adjusted to a value between 6.9 and 7.1 and it is then subjected to a sterile filtration, in order to meet the regulation requirements of the European Pharmacopeia.

Before subjecting an aqueous albumin solution to a chromatography on a stationary phase charged with a compound bearing $C_3$ to $C_8$ alkyl radicals, the corresponding column(s) is(are) equilibrated with an aqueous saline solution having at most 10 times the ionic strength of the aqueous albumin solution. Similarly, before subjecting an aqueous albumin solution to a chromatography on a stationary phase charged with a compound bearing sulfate groups, the corresponding column(s) is(are) equilibrated with a saline solution which is at most isotonic relative to the albumin solution. A sodium chloride solution or phosphate-buffered saline (PBS) is preferably used to equilibrate the chromatography column (s).

In the preferred embodiment, which comprises two or three chromatographies in series, the method according to the invention requires neither any change of buffer during the manipulation nor any change of pH, the various chromatographies being carried out in series.

In the case where the albumin solution treated is a solution of human plasma albumin prepared by the Cohn method or a derived method, the albumin solution obtained is stable, forms practically no polymers under hot conditions and is only very faintly colored, which corresponds to the elimination of the traces of hemoglobin and of heme. When a solution of bovine albumin, for example from the product FLUKA No. 05480, is treated, the albumin obtained is much more stable than the initial albumin. Moreover, it is possible to treat injectable outsize solutions of albumin (for example for clouding or particles) in order once again to impart good stability thereto.

BRIEF DESCRIPTION OF THE DRAWINGS

In order for the subject of the invention to be better understood, one embodiment will now be described, purely as an illustrative example and with no limitation being implied, the characteristics of the product obtained being represented in the attached diagram.

In this diagram.

DETAILED DESCRIPTION

Figure 1A:
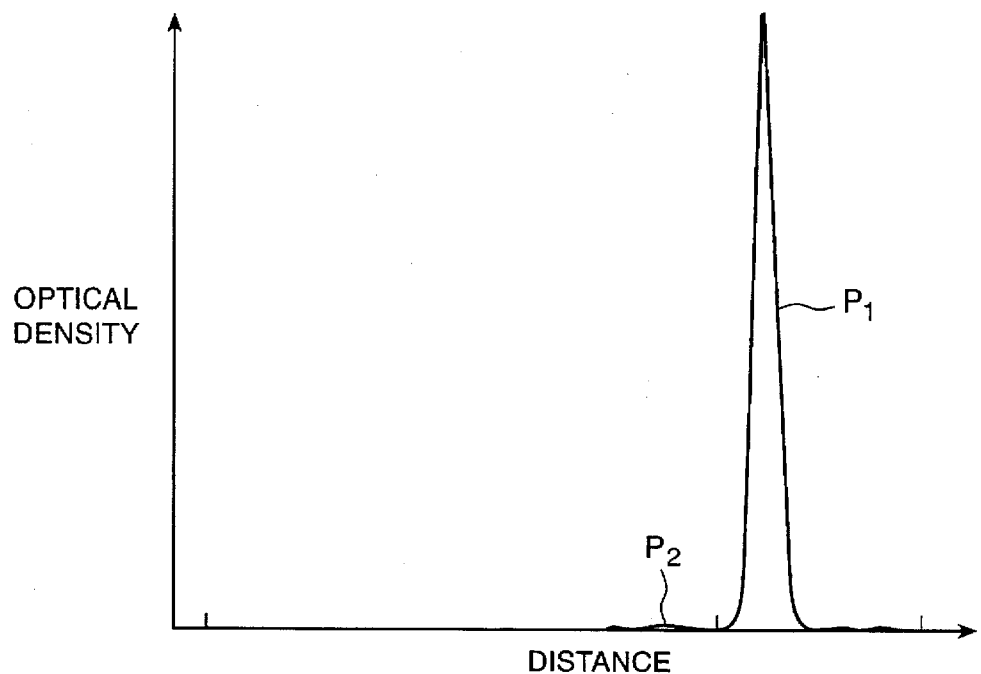
FIG. 1 represents the coloration profiles after electrophoresis on cellulose acetate for an albumin obtained according to the invention (B) and an albumin of the prior art (according to the Cohn process (A))

A human plasma fractionated according to the method described by KISTLER and NITSCHMAN (Vox Sang. 7, 414–424 (1962)) is used as starting material; this method repeats the essential of the Cohn process described above: the starting materials containing the albumin are either supernatant IV or precipitate V.

When starting from supernatant IV, which comprises 40% (by volume) of ethanol and has a pH of 5.85±0.05, the supernatant is diluted to half as much again with NaCl solution at a concentration of 7 g/l. The pH is adjusted to 7.45±0.05 with 1N sodium hydroxide solution. The albumin is pre-concentrated to 90 g/l in an ultrafiltration cassette of "Omega" type (Filtron) used in a "Minisette SS Cell NPT Cell" ultrafiltration system (Filtron Tech. Corp.). This cassette has a filtering surface area of 0.07 $m^2$ and a retention threshold of 30 KDa. Circulation is provided by a peristaltic pump at a pressure which ranges from $2 \times 10^5$ Pa at the start of the operation to $5 \times 10^5$ Pa at the end. When the albumin concentration of 90 g/l has been reached, an NaCl solution of 9 g/l is added to the albumin solution and dialysis is continued to constant volume until an ethanol content of less than 0.1% by volume is obtained. When the ethanol has been thus removed, the dialysis is continued in order to concentrate the solution up to 200 g of albumin per liter. The pH is adjusted 7.10±0.05 with 1N hydrochloric acid solution.

When starting with precipitate V, the said precipitate is resuspended in physiological serum (NaCl solution at a concentration of 9 g per liter) using 4 liters of physiological serum per kilogram of precipitate. Filtration is performed in order to remove the lumps of precipitate not resuspended during the stirring; the pH is adjusted to 7.45±0.05 with 1N sodium hydroxide solution and the solution thus obtained is concentrated up to 90 g of proteins per liter using the same dialysis system as described above for supernatant IV. The dialysis is then continued, adding further physiological serum and working to constant volume, until a final ethanol content of less than 0.1% by volume is obtained. When the ethanol has been thus removed, the dialysis is continued in order to concentrate the solution up to 200 g of proteins per liter. The pH is adjusted to 7.1±0.05 with 1N hydrochloric acid solution.

The albumin solution thus prepared from supernatant IV or from precipitate V then undergoes sterile filtration (0.2 micron "Millex-GS" filter (Millipore)). The raw aqueous solution of albumin which will subsequently be treated by the method according to the invention is thus obtained.

The raw aqueous solution of albumin is first subjected to chromatography on a stationary phase charged with a compound bearing sulfate groups, referred to as polysulfated gel chromatography. This chromatography is performed in a 50 ml column (2.5 cm×10 cm) (Biorad), charged with a particulate material sold by the company SIGMA under the trade name DEXTRAN BEADS SULFATED (matrix of 4% cross-linked beaded dextran). The column is equilibrated beforehand by passing 3 column volumes of physiological serum into the bed. The albumin solution is then conveyed on to this column and the effluent is conveyed directly on to a second chromatography column, on a stationary phase charged with $C_3$ to $C_8$ radicals, referred to as hydrophobic chromatography.

The hydrophobic chromatography is performed in an identical column to the previous column, the chromatography bed of which consists of a particulate material sold by the company MERCK under the trade name "FRACTOGEL TSK BUTYL-650". Before being used, this column is equilibrated by passing 3 column volumes of physiological serum into the chromatography bed. When it has been equilibrated, the hydrophobic chromatography column is connected directly in series to the outlet of the polysulfated gel chromatography column. Equilibration of the two columns may also be carried out in series.

The progress of the chromatography is monitored by measuring the optical density at 280 nm of the fractions emerging from the column. The effluent of the two chromatography columns in series is recovered and then concentrated by dialysis to 200 g of albumin per liter or diluted, in physiological serum, to 40 g of albumin per liter depending on its intended use; the pH is adjusted to 7.00±0.05 and the effluent is subjected to sterile filtration on 0.2 micron "Millex-GS" filters (Millipore). The flow rate in the two columns mounted in series is 16 cm/hour; the chromatographies are carried out at 20° C. By monitoring the progress of the chromatography, it is observed that up to 400 g of albumin may be charged per liter of chromatography bed in the first or in the second column without substantially decreasing the efficiency of the separation.

The polysulfated gel chromatography column bed is regenerated by washing with two column volumes of sodium chloride solution at a concentration of 2 mol per liter, followed by washing with two column volumes of sodium chloride solution at a concentration of i mol per liter, at pH 9. Regeneration of the packing material for the hydrophobic chromatography column is carried out by washing with two column volumes of 0.1 N sodium hydroxide solution.

It is observed that the binding capacity of the chromatography beds was not affected by 40 successive chromatography/regeneration cycles.

Certain characteristics of the albumin obtained by the method according to the invention described above were assessed and the corresponding experimental results are given below. The properties of the aqueous albumin solution were compared before passage on the two polysulfated gel and hydrophobic chromatography columns and after passage on these two columns. The solution before passage is thus an albumin of the prior art and the solution after passage is a chromatographed albumin according to the invention.

A sample is prepared starting with an albumin of the prior art and a sample starting with albumin prepared according to the invention. 10 mg of sodium caprylate is added to these samples per gram of albumin and the sample is heated at 60° C. for 10 hours.

1-Immunoelectrophoresis:

The GRABAR method was used (Grabar P. et al., Biochem. Biophys. Acta, 17, 67–75 (1955)). Total antiserum was prepared by immunizing a horse with complete human plasma. For the albumin of the prior art, the presence of a line of precipitation is observed around the deposit reservoir, which corresponds to the presence of "neo=antigens" consisting of denatured proteins; by contrast, this line of precipitation does not exist for the chromatographed albumin according to the invention, which demonstrates that the method according to the invention enables the albumin to be separated from the contaminant proteins constituting impurities.

Figure 1B:
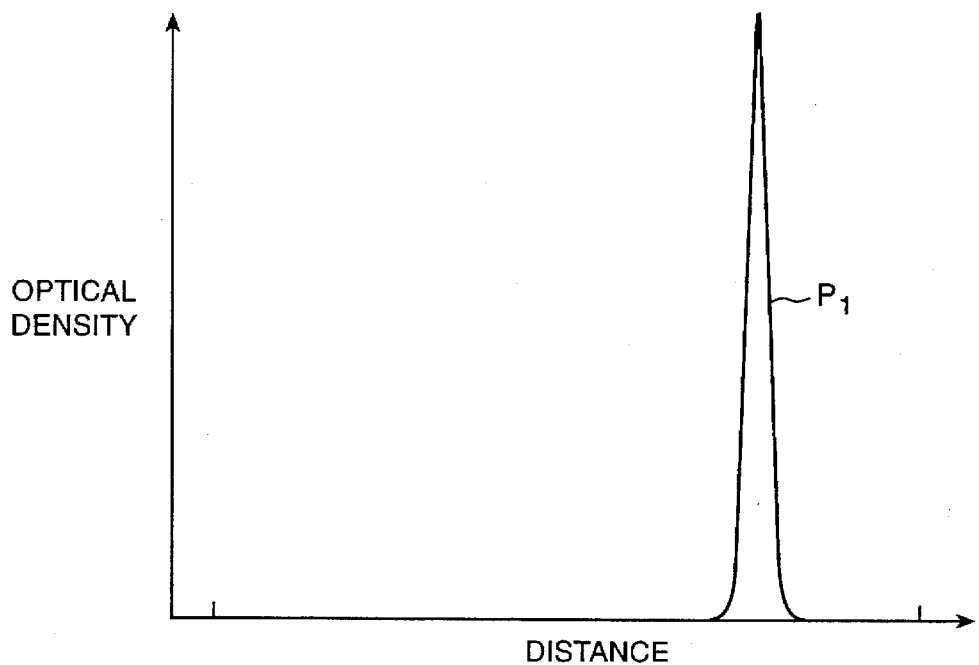

2-Electrophoresis on a cellulose acetate membrane:

5% protein solutions were tested as described in the article ROELANDS J. F. et al., Vox Sang., 26, 415–424 (1974). The samples were tested at 220 volts for 35 minutes with a "TRIS-VERONAL" buffer at pH 9.2 and at an ionic strength of 0.05. The membranes were visualized with "PONCEAU S" dye and quantification was made by densitometry. The resultant curves are given in FIG. 1: on the graph labeled A, there is observed, next to the main peak $P_1$ which corresponds to albumin, a secondary peak $P_2$ which corresponds to impurities, whereas on graph B which corresponds to the albumin according to the invention, peak $P_1$ is found as before but the peak $P_2$ has disappeared, which shows the efficiency of the purification method according to the invention.

3-Gel filtration:

A "Biorad" column (1.5×50 cm) with "SEPHACRYL S 400 HR" packing material sold by the company "PHARMACIA LKB BIOTECHNOLOGY" is used. This column is equilibrated beforehand with phosphate buffer at pH 7. 20 mg of albumin from each sample are subsequently passed on to the prepared column; the flow rate is 1 ml per minute. The optical absorption at 280 nm is monitored for the chromatographic fractions (1.2 ml per fraction) using a "Uvicon 810" spectrophotometer.

Figure 2:
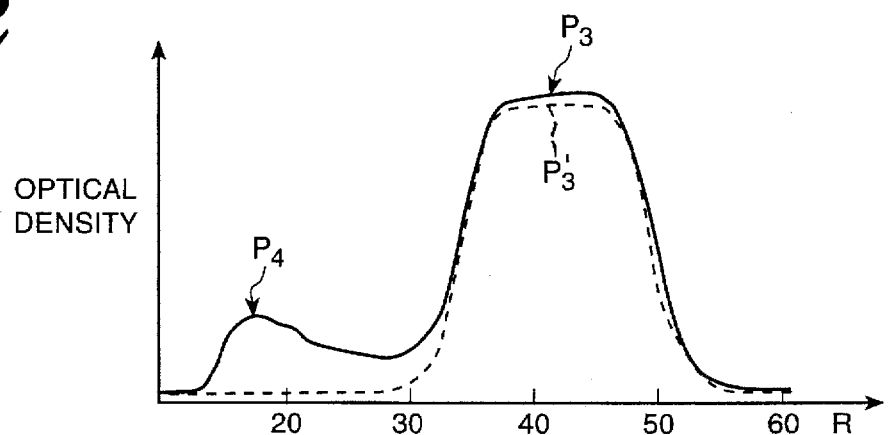
FIG. 2 represents the optical density absorption curves obtained by gel filtration for an albumin obtained according to the invention and an albumin of the prior art (according to the Cohn process)

The experimental curves obtained are represented in FIG. 2. The solid-line curve corresponds to the albumin of the prior art and shows, next to the peak $P_3$ corresponding to albumin, a peak $P_4$ corresponding to contaminant impurities, including polymers. By contrast, the dotted-line curve corresponds to the albumin obtained according to the invention and, on this curve, the peak $P'_3$, which is very close to $P_3$, corresponds to albumin but there is no neighbouring peak, which demonstrates the absence of contaminant impurity.

Figure 3:
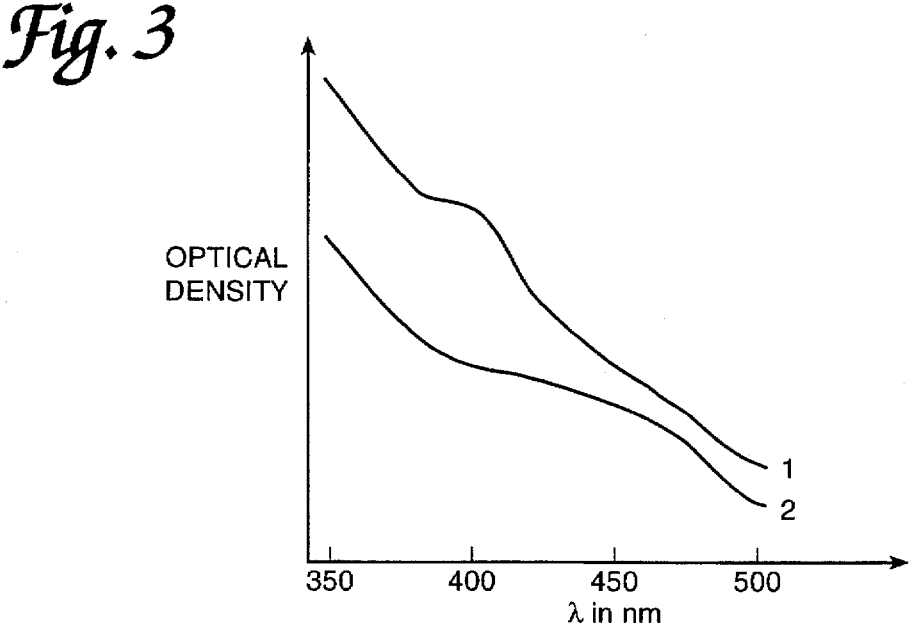
FIG. 3 represents the optical density spectrum obtained for an albumin obtained according to the invention and an albumin of the prior art (according to the Cohn process)

4-Optical density spectrum:

The optical density spectrum was studied between 350 and 500 nm for a sample of albumin of the prior art and a sample of albumin obtained according to the invention (curves 1 and 2 respectively of FIG. 3). It is observed that, for the albumin obtained according to the invention, there is absence of absorption at 403 nm, in contrast to that which is found for the other sample. It is known that hemoglobin absorbs at a lambda wavelength equal to 403 nm. It may thus be stated that the albumin of the prior art contains traces of hemoglobin, which are not found in the albumin obtained according to the invention; the latter effectively has a less intense color, even after heating for 10 hours at 60° C. with a stabilization additive.

5-Variation in turbidity:

The variation in the turbidity was studied as a function of the heating time at 60° C. for the albumin of the prior art and the albumin obtained according to the invention. The two samples were subjected to an addition of 1% by weight of sodium caprylate relative to the weight of albumin.

Figure 4:
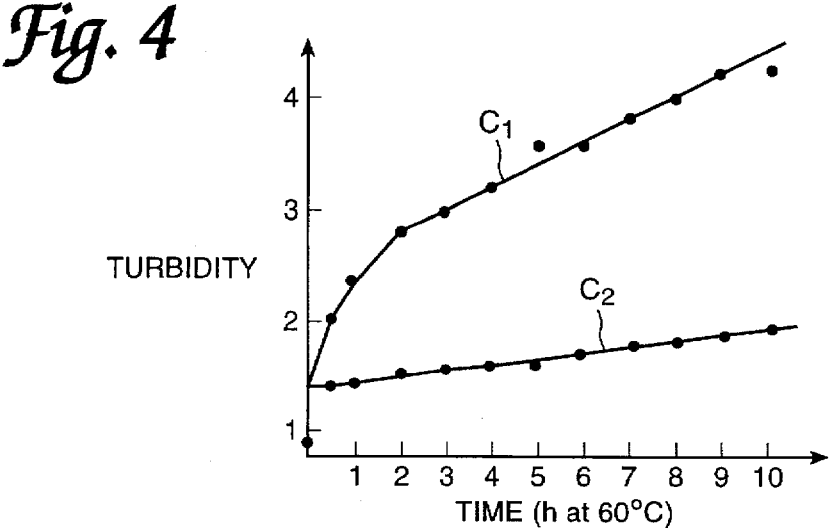
FIG. 4 represents the variation in the turbidity as a function of the heating time at 60° C. for an albumin obtained according to the invention and an albumin of the prior art (according to the Cohn process).

FIG. 4 shows that the sample of albumin of the prior art (curve $C_1$) has a turbidity which develops fairly rapidly with time, in contrast with the sample of albumin according to the method (curve $C_2$). This variation in turbidity corresponds to the formation of polymers. It is thus observed that the removal of the albumin contaminants results in the reduction of the formation of the polymers, which appear after heating at 60° C. for 10 hours and during prolonged storage of the albumin solutions despite the addition of stabilizing agents, such as sodium caprylate. The preparation method according to the invention leads to an albumin solution with a much lower level of polymer formation, which is particularly advantageous from a commercial point of view.

We claim:

1. A chromatographic separation method for purifying an aqueous solution of albumin containing contaminant proteins comprising binding the contaminant proteins in said solution to a solid stationary chromatography phase and collecting purified albumin as an effluent, said solid stationary chromatography phase being neutral and containing at least one compound containing $C_3$ to $C_8$ alkyl radicals or a sulfate group.

2. The method according to claim 1 wherein said solid stationary chromatography phase comprises particles having an average size of between 1 µm and 2mm.

3. The method according to claim 1 wherein said albumin is derived from dialyzed, fractionated human blood plasma, said fractionation comprising variations in temperature and addition of precipitating agents to remove factor VIII, factor IX and γ-globulin, and said dialysis comprising removal of said precipitating agents.

4. The method according to claim 1 wherein said alkyl radicals are butyl radicals.

5. The method according to claim 1 wherein said compound containing a sulfate group is dextran sulfate.

6. The method of claim 1 wherein said solution has a flow rate through said solid stationary chromatography phase of between 1 and 30 cm/hr.

7. The method according to claim 1 wherein said binding is accomplished at a temperature of between 1 and 30° C.

8. The method according to claim 1 wherein said aqueous solution contains between 1 g and 300g albumin per liter and has a pH of between 6 and 8.

9. The method according to claim 8 wherein the pH of said solution is between 6.9 and 7.1.

10. The method according to claim 1 further comprising equilibrating said solid stationary chromatography phase containing at least one compound containing $C_3$ to $C_8$ alkyl radicals with an aqueous solution having at most 10 times the ionic strength of said solution of albumin, prior to said binding.

11. The method of claim 10 wherein said equilibrating comprises adding a sodium chloride solution or a phosphate buffer to said solid phase.

12. The method according to claim 1, further comprising equilibrating said solid stationary chromatography phase containing at least one compound containing a sulfate group with aqueous solution which is, at most, isotonic relative to said solution of albumin, prior to said binding.

13. The method of claim 12 wherein said equilibrating comprises adding a sodium chloride solution or a phosphate buffer to said solid phase.

14. The method according to claim 1 wherein said binding comprises subjecting the aqueous solution of albumin to at least two chromatographic separations, at least one separation comprising a stationary phase containing a compound containing $C_3$ to $C_8$ alkyl radicals and at least one separation comprising a stationary phase containing a compound containing a sulfate group.

15. The method according to claim 14 wherein said chromatographic separation comprising a stationary phase of $C_3$ to $C_8$ alkyl radicals follows said chromatographic separation comprising a stationary phase containing a sulfate group.

16. The method according to claim 14 wherein chromatographic separations comprising a stationary phase of $C_3$ to $C_8$ alkyl radicals precedes and follows said chromatographic separation comprising a stationary phase containing a sulfate group.

17. The method according to claim 14 wherein chromatographic separations comprising a stationary phase containing a sulfate group precedes and follows said chromatographic separation comprising a stationary phase of $C_3$ to $C_8$ alkyl radicals.

18. The method of claim 14 wherein the effluent of a first of said at least two separations is supplied directly to a subsequent separation.

* * * * *